(12) United States Patent
Yoshida et al.

(10) Patent No.: US 8,003,790 B2
(45) Date of Patent: Aug. 23, 2011

(54) SALT OF PROLINE DERIVATIVE, SOLVATE THEREOF, AND PRODUCTION METHOD THEREOF

(75) Inventors: Tomohiro Yoshida, Tokyo (JP); Hiroshi Sakashita, Tokyo (JP); Naoko Ueda, Tokyo (JP); Shinji Kirihara, Tokyo (JP); Satoru Uemori, Tokyo (JP); Reiko Tsutsumiuchi, Tokyo (JP); Fumihiko Akahoshi, Tokyo (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 486 days.

(21) Appl. No.: 11/816,493

(22) PCT Filed: Feb. 17, 2006

(86) PCT No.: PCT/JP2006/302827
§ 371 (c)(1),
(2), (4) Date: Oct. 11, 2007

(87) PCT Pub. No.: WO2006/088129
PCT Pub. Date: Aug. 24, 2006

(65) Prior Publication Data
US 2009/0216016 A1    Aug. 27, 2009

(30) Foreign Application Priority Data
Feb. 18, 2005 (JP) .................................. 2005-041851

(51) Int. Cl.
*C07D 417/14* (2006.01)
(52) U.S. Cl. .................................. 544/369; 514/254.02
(58) Field of Classification Search .................. None
See application file for complete search history.

(56) References Cited

U.S. PATENT DOCUMENTS

| 5,939,560 | A | 8/1999 | Jenkins et al. |
| 6,303,661 | B1 | 10/2001 | Demuth et al. |
| 7,074,794 | B2 | 7/2006 | Kitajima et al. |
| 2004/0106655 | A1 | 6/2004 | Kitajima et al. |
| 2004/0259883 | A1* | 12/2004 | Sakashita et al. ........ 514/254.05 |

FOREIGN PATENT DOCUMENTS

| EP | 1 308 439 A8 | 5/2003 |
| EP | 1 882 474 A1 | 1/2008 |
| EP | 1 894 567 A1 | 3/2008 |
| WO | WO 97/40832 A1 | 11/1997 |
| WO | WO 98/19998 A2 | 5/1998 |
| WO | WO 01/55105 A1 | 8/2001 |
| WO | WO 02/02560 A2 | 1/2002 |
| WO | WO 02/14271 A1 | 2/2002 |
| WO | WO 02/062764 A1 | 8/2002 |

OTHER PUBLICATIONS

"ICH Guideline for Residual Solvents Q3C" Kojima, 1997, available at: http://www.nihs.go.jp/drug/ich_q3c_step4/q3cdrf_9.html, Dec. 12, 2009.*
Weber et al., *J. Med. Chem.*, 47(17): 4135-4141 (2004).
Myerson, Allan S. (Ed.), Handbook of Industrial Crystallization, $2^{nd}$ Edition, Butterworth-Heinemann 2002, pp. 132-133, 141-148, and 161-167.
International Conference on Harmonisation of Technical Requirements for the Registration of Pharmaceuticals for Human Use, "Impurities: Guideline for Residual Solvents" (Q3C(R3))—Current Step 4 Version) (Nov. 2005).

* cited by examiner

*Primary Examiner* — Emily Bernhardt
(74) *Attorney, Agent, or Firm* — Leydig, Voit & Mayer, Ltd.

(57) ABSTRACT

The present invention provides 3-{(2S,4S)-4-[4-(3-methyl-1-phenyl-1H-pyrazol-5-yl)piperazin-1-yl]pyrrolidin-2-ylcarbonyl}thiazolidine (compound I) useful as a dipeptidyl peptidase-IV inhibitor, which has superior properties of stability and hygroscopicity, and reproducible crystal structure, and a production method thereof.

8 Claims, 5 Drawing Sheets

SALT OF PROLINE DERIVATIVE, SOLVATE THEREOF, AND PRODUCTION METHOD THEREOF

TECHNICAL FIELD

The present invention relates to a novel salt of 3-{(2S,4S)-4-[4-(3-methyl-1-phenyl-1H-pyrazol-5-yl)piperazin-1-yl]pyrrolidin-2-ylcarbonyl}thiazolidine useful as a dipeptidyl peptidase-IV (hereinafter to be referred to as DPP-IV) inhibitor, and a solvate thereof.

BACKGROUND ART

DPP-IV inhibitors inhibit inactivation of glucagon-like peptide-1 (hereinafter to be referred to as GLP-1) in plasma, and potentiate their incretin action. Therefore, they are useful as therapeutic drugs for diabetes and the like, and under research and development as drugs potentially effective for the treatment of diabetes, particularly type 2 diabetes (see, patent references 1 to 6, non-patent reference 1).

A series of compounds have been reported as useful thiazolidine derivatives. (see, patent reference 7). Of the Example compounds described in this reference, 3-{(2S,4S)-4-[4-(3-methyl-1-phenyl-1H-pyrazol-5-yl)piperazin-1-yl]pyrrolidin-2-ylcarbonyl}thiazolidine is noteworthy (hereinafter to be referred to as compound I). While compound I is described in the form of a 3 hydrochloride, this salt has pharmaceutically undesirable properties from the aspects of stability and hygroscopicity, and production in the same form with reproducibility has been found to be difficult. Particularly, to satisfy the regulatory requirements in the development of pharmaceutical products, a compound of certain quality needs to be produced with reproducibility. Therefore, these properties observed in 3 hydrochloride of compound I are considered to be disadvantageous for the development of pharmaceutical products.

Moreover, while this reference (patent reference 7) discloses particular salts of "compound I" and other thiazolidine derivatives as Example compounds, no discussion is found over a polymorphic crystal of any of the Example compounds.

An ability of a substance to crystallize into two or more kinds of crystal structures is known as polymorphism, and individual crystal forms are called polymorphic crystal. Various polymorphic crystals of a single compound sometimes show completely different properties of preservation stability, solubility and the like. Such difference in the properties may result in the difference in the action effect. In view of such differences, study of individual polymorphic crystals and a mixture of polymorphic crystals is particularly useful for the development of pharmaceutical products.

There are multiple notations of polymorphic crystals depending on the nomenclature, such as Form A, Form B, Form I, Form II, Form α, Form β and the like. In these notations, "Type" (Type A etc.) may be used instead of "Form". In any event, both notations are used to mean the same.

However, it is not always easy to find various polymorphic crystals of a certain compound. Once the presence of a particular polymorphic crystal is acknowledged and the characteristics thereof are considered to be preferable, the workers need to find a method to always supply the polymorphic crystal constantly in a large amount as single crystals. It is not easy to establish a method of supplying a single crystal or substantially single crystal of a certain polymorphic crystal, and intensive studies are required.

Patent reference 1: WO97/040832
Patent reference 2: WO98/019998
Patent reference 3: U.S. Pat. No. 5,939,560
Patent reference 4: WO01/055105
Patent reference 5: WO02/002560
Patent reference 6: WO02/062764
Patent reference 7: WO02/014271
Non-patent reference 1: J. Med. Chem., 47(17), 4135-4141 (2004)

DISCLOSURE OF THE INVENTION

The problem of the present invention is to find, with respect to compound I, compounds having superior properties in terms of stability, solubility, hygroscopicity, bioavailability and the like desired for producing pharmaceutical products and a reproducible crystal structure, as well as to provide a method for producing them.

The present inventors have prepared salts of compound I with mono-, di- and tri-basic acids, characterized crystals of individual salts and solvates thereof, and found novel salts of compound I having preferable properties in terms of stability and hygroscopicity. They have further conducted intensive studies and found a stable industrial production method of the novel salt of the present invention, which resulted in the completion of the present invention.

Accordingly, the gist of the present invention rests in the salts, solvates thereof, and production methods thereof, of the following (1) to (33).

(1) A salt of 3-{(2S,4S)-4-[4-(3-methyl-1-phenyl-1H-pyrazol-5-yl)piperazin-1-yl]pyrrolidin-2-ylcarbonyl}thiazolidine with an organic or inorganic mono-, di- or tri-basic acid, or a solvate thereof.

(2) The salt of the above-mentioned (1), wherein the organic or inorganic monobasic acid is hydrochloric acid, hydrobromic acid, nitric acid, mesyl acid, tosyl acid, besyl acid, naphthalene-1-sulfonic acid, naphthalene-2-sulfonic acid, gallic acid or camphorsulfonic acid, or a solvate thereof, provided that when the monobasic acid is hydrochloric acid, then the salt should be 2 or 2.5 hydrochloride.

(3) The salt of the above-mentioned (1), wherein the organic or inorganic dibasic acid is fumaric acid, maleic acid, sulfuric acid, succinic acid, L-tartaric acid, ethanedisulfonic acid or citric acid, or a solvate thereof.

(4) The salt of the above-mentioned (1), wherein the organic or inorganic tribasic acid is phosphoric acid, or a solvate thereof.

(5) The salt of the above-mentioned (1), which is a salt with 2.0 hydrobromic acid, 2.5 hydrobromic acid, 2 maleic acid, 2 tosyl acid, 2 besyl acid, 2 hydrochloric acid, 2.5 hydrochloric acid, 2 naphthalene-1-sulfonic acid, 2 naphthalene-2-sulfonic acid, 2 camphorsulfonic acid, fumaric acid, sulfuric acid, succinic acid, L-tartaric acid or citric acid, or a solvate thereof.

(6) The salt of the above-mentioned (1), which is a salt with 2.0 hydrobromic acid, 2.5 hydrobromic acid, 2 maleic acid, 2 tosyl acid, 2.5 hydrochloric acid, 2 naphthalene-1-sulfonic acid, 2 mesyl acid, 3 mesyl acid or 2 naphthalene-2-sulfonic acid, or a solvate thereof.

(7) A salt of 3-{(2S,4S)-4-[4-(3-methyl-1-phenyl-1H-pyrazol-5-yl)piperazin-1-yl]pyrrolidin-2-ylcarbonyl}thiazolidine with a monobasic acid, which has a solubility in water of 7 mg/mL to 2 g/mL at ambient temperature, or a solvate thereof.

(8) The salt of the above-mentioned (7), which has a solubility in water of not less than 20 mg/mL at 37° C., or a solvate thereof.

(9) The salt of the above-mentioned (7), which has a solubility in water of 7 mg/mL at pH 9 to 12, or a solvate thereof.

(10) The salt of the above-mentioned (1), which shows hygroscopicity of not more than 6% as measured at 25° C., or a solvate thereof.

(11) The salt of the above-mentioned (10), which shows hygroscopicity of 5% as measured at relative humidity within the range of 0% to 50% at 25° C., or a solvate thereof.

(12) The salt of the above-mentioned (10), which shows hygroscopicity of 2% as measured at relative humidity within the range of 5% to 90% at 25° C., or a solvate thereof.

(13) The salt of any of the above-mentioned (10) to (12), which is a salt with the monobasic acid of the above-mentioned (2), or a solvate thereof.

(14) 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide, or a solvate thereof.

(15) The salt of the above-mentioned (14), which has peaks at diffraction angles represented by 2θ of 5.4°, 13.4° and 14.4° (each ±0.2°) in a powder X-ray diffraction pattern, or a hydrate thereof.

(16) The hydrate of the above-mentioned (15), which is a 1.0 to 2.0 hydrate.

(17) The salt of the above-mentioned (14), which has peaks at diffraction angles represented by 2θ of 5.4°, 13.4°, 14.4°, 22.6° and 26.5° (each ±0.2°) in a powder X-ray diffraction pattern, or a hydrate thereof.

(18) The hydrate of the above-mentioned (17), which is a 1.0 to 2.0 hydrate.

(19) The salt of the above-mentioned (14), which shows a powder X-ray diffraction pattern as illustrated in FIG. 1, or a hydrate thereof.

(20) 3-{(2S,4S)-4-[4-(3-methyl-1-phenyl-1H-pyrazol-5-yl)piperazin-1-yl]pyrrolidin-2-ylcarbonyl}thiazolidine 2.0 hydrobromide, or a solvate thereof.

(21) A hydrate of the salt of the above-mentioned (20), which has peaks at diffraction angles represented by 2θ of 5.7°, 7.7°, 11.3°, 16.2° and 17.0° (each ±0.2°) in a powder X-ray diffraction pattern.

(22) A hydrate of the salt of the above-mentioned (20), which has peaks at diffraction angles represented by 2θ of 5.2°, 10.4°, 19.1°, 19.8° and 20.7° (each ±0.2°) in a powder X-ray diffraction pattern.

(23) A hydrate of the salt of the above-mentioned (20), which has peaks at diffraction angles represented by 2θ of 5.5°, 13.4°, 14.3°, 21.4° and 26.7° (each ±0.2°) in a powder X-ray diffraction pattern.

(24) A hydrate of the salt of the above-mentioned (20), which shows a powder X-ray diffraction pattern as illustrated in FIG. 2.

(25) A hydrate of the salt of the above-mentioned (20), which shows a powder X-ray diffraction pattern as illustrated in FIG. 3.

(26) A hydrate of the salt of the above-mentioned (20), which shows a powder X-ray diffraction pattern as illustrated in FIG. 4.

(27) A method of producing 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide or a solvate thereof, which comprises eliminating 1,1-dimethylethyloxycarbonyl from 3-{(2S,4S)-1-(1,1-dimethylethyloxycarbonyl)-4-[4-(3-methyl-1-phenyl-1H-pyrazol-5-yl)piperazin-1-yl]pyrrolidin-2-ylcarbonyl}thiazolidine with hydrobromic acid, and simultaneously forming a salt.

(28) A method of producing 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide or a solvate thereof, which comprises crystallizing 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide from an acceptable solvent.

(29) The method of the above-mentioned (28), wherein the acceptable solvent is water, and/or a solvent selected from the solvents falling under the permitted daily exposure ("PDE") of above 10 mg/day in the "ICH guideline of residual solvent Q3C".

(30) The method of the above-mentioned (28), wherein the acceptable solvent is water, and/or a solvent selected from the solvents falling under class 3 in the "ICH guideline of residual solvent Q3C".

(31) The method of the above-mentioned (28), wherein the acceptable solvent is a solvent selected from ethanol, 1-propanol, 2-propanol, ethyl acetate and acetone.

(32) The method of the above-mentioned (28), wherein the acceptable solvent is ethanol and/or water.

(33) A 1.0 to 2.0 hydrate of 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide.

EFFECT OF THE INVENTION

The salts of compound I, solvates thereof and novel polymorphic crystals thereof have one or more properties selected from improved stability, improved hygroscopicity (deliquescency), rapid isolation from solvent and easy production of preparation, which promotes the development of compound I as a pharmaceutical product.

BEST MODE FOR EMBODYING THE INVENTION

Figure 1:
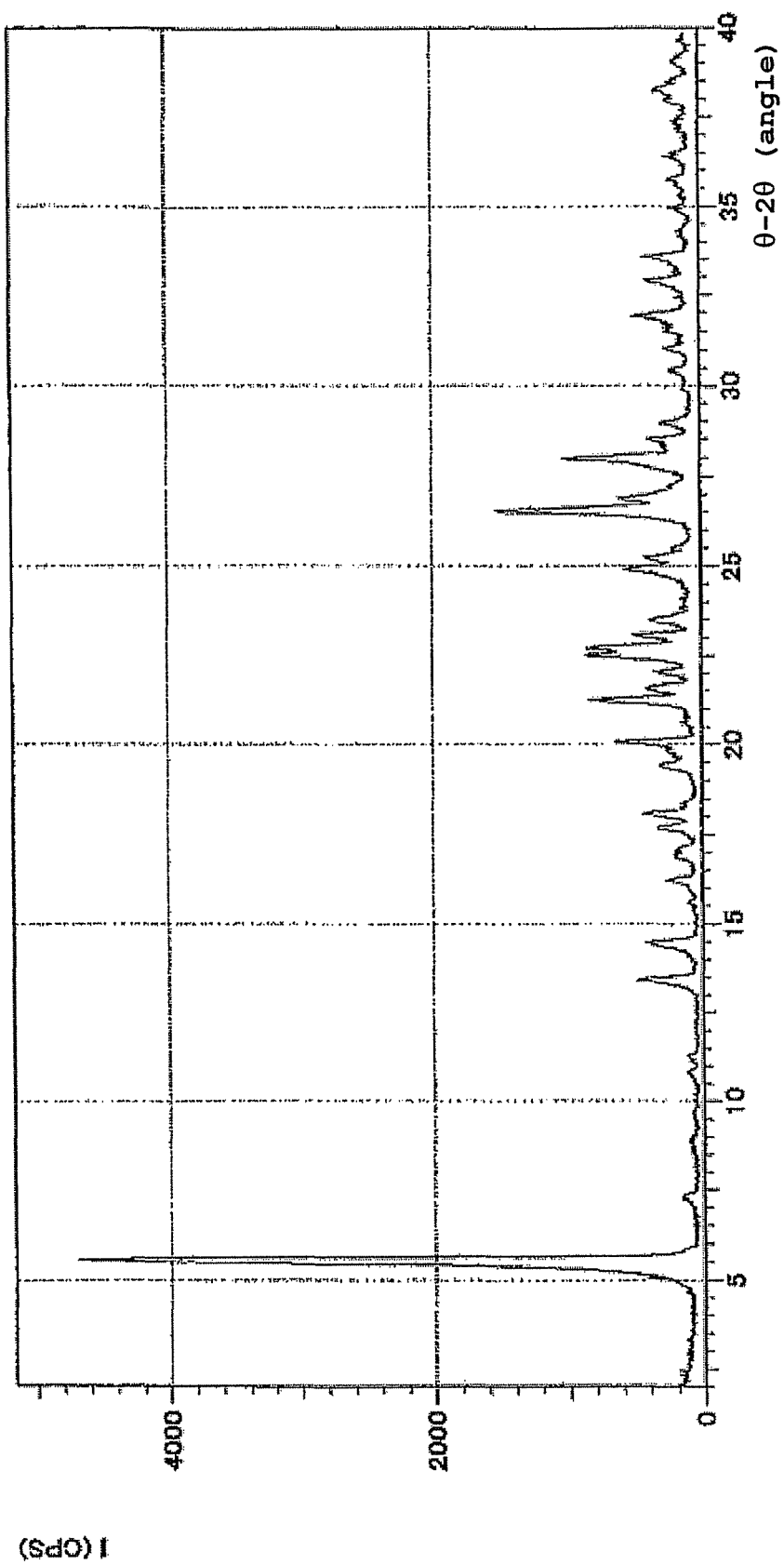
FIG. 1 shows the measurement results of the powder X-ray diffraction of the title compound of Example 4, wherein the Y axis shows diffraction intensity and the axis of abscissas shows diffraction angle (2θ).

3-{(2S,4S)-4-[4-(3-Methyl-1-phenyl-1H-pyrazol-5-yl)piperazin-1-yl]pyrrolidin-2-ylcarbonyl}thiazolidine (compound I) is shown in the following.

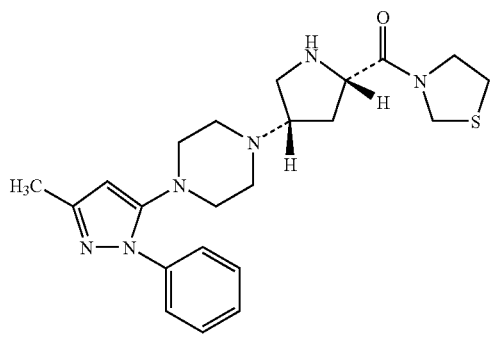

The 3 hydrochloride of compound I can be produced according to the synthesis method described as Example 222 of WO02/14271. This compound can be converted to a free base using a suitable base. As the base to be used, alkali metal or alkaline earth metal carbonates (sodium hydrogencarbonate, sodium carbonate, potassium carbonate etc.), alkali metal or alkaline earth metal hydroxides (sodium hydroxide, potassium hydroxide etc.) and the like can be mentioned.

Compound I can be obtained, for example, by adding the compound of Example 222 to an aqueous solution of any base mentioned above, and extracting the mixture with a hydrocarbon solvent (benzene, toluene etc.), a halogenated hydrocarbon solvent (dichloromethane, dichloroethane, chloroform, carbon tetrachloride etc.), ethyl acetate and the like.

Moreover, 2.5 hydrobromide of compound I can also be produced according to the following scheme.

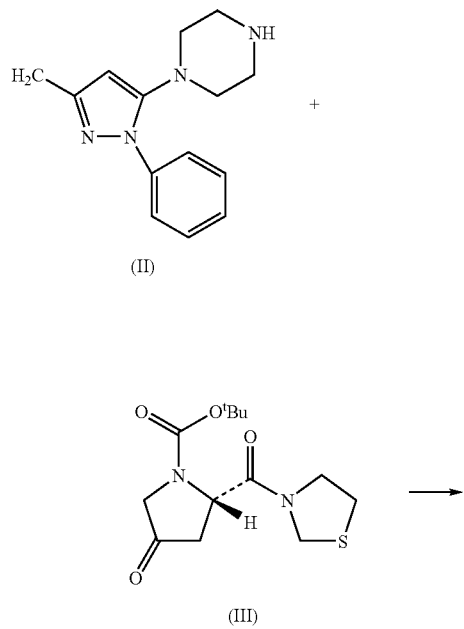

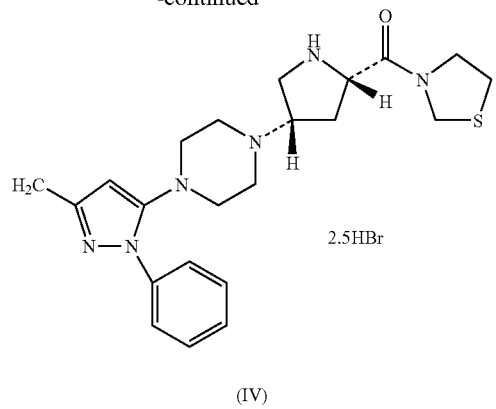

2.5 Hydrobromide (IV) of compound I can be obtained by subjecting 3-[(2S)-1-(1,1-dimethylethyloxycarbonyl)-4-oxopyrrolidin-2-ylcarbonyl]thiazolidine (III) to reductive amination with 1-(3-methyl-1-phenyl-1H-pyrazol-5-yl)piperazine (II) or a salt thereof, and then eliminating 1,1-dimethylethyloxycarbonyl from the resulting compound with hydrobromic acid.

The reductive amination is carried out using about 0.5 to 10 mol, preferably about 1 to 2 mol, of the compound represented by the formula (III) and about 0.5 to 10 mol, preferably about 1 to 2 mol, of metal hydrogen complex compound (composite hydrogen compound such as sodium borohydride, sodium cyanoborohydride, sodium triacetoxyborohydride and the like; diborane etc.), both per 1 mol of the compound represented by the formula (II) or a salt thereof, in an inert solvent and, where necessary, in the presence of an acidic catalyst (acetic acid, p-toluenesulfonic acid, boron trifluoride-diethyl ether complex etc.). As the inert solvent, alcohols (methanol, ethanol, 1-propanol, 2-propanol (hereinafter to be referred to as IPA), butanol etc.), nitriles (acetonitrile, propionitrile etc.), amides (formamide, N,N-dimethylformamide, N,N-dimethylacetamide, 1,3-dimethyl-2-imidazolidinone etc.), ethers (diethyl ether, diisopropyl ether, t-butyl methyl ether, 1,4-dioxane, tetrahydrofuran (hereinafter to be referred to as THF) etc.), halogenated hydrocarbons (dichloromethane, chloroform, 1,2-dichloroethane etc.), hydrocarbons (n-hexane, cyclohexane, benzene, toluene etc.), a mixed solvent of any of them and the like can be mentioned.

The reaction temperature is −20° C. to 200° C., preferably 0° C. to 80° C., and the reaction time is about 0.5 to 96 hrs, preferably 0.5 to 24 hrs.

By reacting, without isolation and purification, the resultant product of this reaction with 1 to 20 mol, preferably about 2.5 to 5 mol, of hydrobromic acid per 1 mol of compound represented by the formula (II) or a salt thereof, in water, an alcohol (methanol, ethanol, IPA etc.), an ether (THF, dioxane etc.), a halogenated hydrocarbon (dichloromethane, dichloroethane, chloroform etc.), ethyl acetate, acetonitrile and the like, or a mixed solvent of any of them, 2.5 hydrobromide of compound I can be obtained.

The reaction temperature is −20° C. to 200° C., preferably 0° C. to 100° C., and the reaction time is about 0.5 to 48 hrs, preferably 0.5 to 24 hrs. After the reaction, the precipitate is collected by filtration to give the salt represented by the formula (IV).

In the present invention, hydrochloride, hydrobromide, nitrate, mesylate, maleate, tosylate, besylate, naphthalene-1-sulfonate, naphthalene-2-sulfonate, gallate, (+)-camphorsulfonate, (−)-camphorsulfonate, fumarate, sulfate, succinate, L-tartrate, ethanedisulfonate, citrate or phosphate of compound I (hereinafter to be also referred to as "the salt of the present invention") is optically pure and, for example, optical purity of (2S,4S)-enantiomer is not less than 90% enantiomer excess (hereinafter to be referred to as e.e.), preferably not less than 95% e.e., more preferably not less than 99% e.e.

The form of the salt of the present invention is not particularly limited, and the salt may be an oil, an amorphous form or a crystal. Preferred form of the salt is a crystal.

As the salt in the form of crystal, 2.0 hydrochloride, 2.5 hydrochloride, 2 hydrobromide, 2.5 hydrobromide, 2 mesylate, 3 mesylate, 2 tosylate, 2 besylate, 2 naphthalene-1-sulfonate, 2 naphthalene-2-sulfonate, 2 (+)-camphorsulfonate, 2 maleate, 2 fumarate, 2 L-tartrate and the like can be mentioned. These salts can also be characterized by the diffraction peaks of the powder X-ray diffraction pattern.

In the present invention, the polymorphic crystal of 2.0 hydrobromide is referred to as Form A, Form B or Form C. In addition, the polymorphic crystal of 2 tosylate is referred to as Form A, Form B or Form C, the polymorphic crystal of 2 besylate is referred to as Form A or Form B, the polymorphic crystal of 2 maleate is referred to as Form A or Form B, and the polymorphic crystal of 2 fumarate is referred to as Form A or Form B.

The solvate of the salt of the present invention can be present as hemi-, mono-, di-, tri, tetra-, penta-, hexa-solvates and the like. The solvent used for crystallization, such as alcohol (methanol, ethanol, IPA etc.), aldehyde, ketone (acetone etc.) or ester (ethyl acetate etc.) etc. and water contained in these solvents can be incorporated into the crystal lattice. In general, it is impossible to predict whether a compound becomes a solvate or a non-solvate during crystallization and production step thereafter. It depends on the combination of compound, production conditions and various interactions with a solvent selected, particularly water. Moreover, the stability of a crystal and an amorphous form of a salt of a certain compound or a solvate thereof can only be confirmed by actually measuring values.

The salt of the present invention may be a solvate with a solvent (water, an organic solvent etc.) or a non-solvate. In other words, the salt of the present invention may be a hydrate or a non-hydrate. When it is a hydrate, the amount of water for hydration may vary depending on various conditions. It is preferably a not more than 2.0 hydrate, more preferably a 1.0 to 2.0 hydrate.

The salt of the present invention can contain a solvent safe for mammals (pharmaceutically, pharmacologically or physiologically acceptable salt etc.), or a solvate with a solvent. The "solvent" is selected from those falling under the permitted daily exposure ("PDE") of above 10 mg/day in the "ICH guideline of residual solvent Q3C" and/or those falling under class 3 in the "ICH guideline of residual solvent Q3C". To be specific, ethanol, 1-propanol, IPA, 1-butanol, 2-butanol, 1-pentanol, acetic acid, methyl acetate, ethyl acetate, propyl acetate, isopropyl acetate, n-butyl acetate, isobutyl acetate, formic acid, ethyl formate, acetone, methyl ethyl ketone, methyl isobutyl ketone, heptane, pentane, diethyl ether, t-butyl methyl ether, THF, anisole, cumene, dimethyl sulfoxide and the like can be mentioned. Of these solvents, ethanol is preferable. The content of the "solvent" is not more than 50000 ppm, preferably not more than 5000 ppm.

The salt of the present invention can be produced according to a method known per se. For example, the salt of the present invention can be obtained by reacting compound I with an organic acid or inorganic acid selected from hydrochloric acid, hydrobromic acid, nitric acid, mesyl acid, maleic acid, tosyl acid, besyl acid, naphthalene-1-sulfonic acid, naphthalene-2-sulfonic acid, gallic acid, (+)-camphorsulfonic acid, (−)-camphorsulfonic acid, fumaric acid, sulfuric acid, succinic acid, L-tartaric acid, ethanedisulfonic acid, citric acid and phosphoric acid.

This reaction is generally carried out in an inert solvent or without solvent. As the "inert solvent", water, alcohols (methanol, ethanol, 1-propanol, IPA, butanol etc.), ketones (acetone, methyl ethyl ketone etc.), nitriles (acetonitrile, propionitrile etc.), amides (formamide, N,N-dimethylformamide, N,N-dimethylacetamide, 1,3-dimethyl-2-imidazolidinone etc.), ethers (diethyl ether, diisopropyl ether, t-butyl methyl ether, 1,4-dioxane, THF etc.), esters (ethyl formate, ethyl acetate, propyl acetate etc.), halogenated hydrocarbons (dichloromethane, chloroform, 1,2-dichloroethane etc.), hydrocarbons (n-hexane, cyclohexane, benzene, toluene etc.), sulfoxides (dimethyl sulfoxide etc.), polar solvents (sulfolane, hexamethylphosphorylamide etc.), a mixed solvent of any of them and the like can be mentioned. Of these solvents, water, mixed solvents of water and an alcohol (mixed solvent of water and methanol, mixed solvent of water and ethanol, mixed solvent of water and 1-propanol, mixed solvent of water and IPA, etc.) are preferable.

The "inert solvent" is generally used in an amount of 1 to 100 w/v %, preferably 2 to 50 w/v %, relative to compound I.

The reaction temperature is generally from −20° C. to the refluxing temperature of the solvent, preferably from 0° C. to the refluxing temperature of the solvent. The reaction time is generally about 1 min to 24 hrs, preferably about 10 min to 6 hrs, more preferably about 30 min to 3 hrs.

The thus-obtained salt can be isolated and purified from the reaction mixture according to separation means known per se (concentration, concentration under reduced pressure, solvent extraction, crystallization, recrystallization, phase transfer, chromatography etc.).

A salt of compound I can be obtained in the form of a crystal by crystallizing the thus-obtained salt. As the crystallization method, methods known per se can be mentioned, and crystallization from a solution, crystallization from a vapor, crystallization from a molten form can be mentioned (see, A. S. Myerson Ed., Handbook of Industrial Crystallization Second Edition, Butterworth-Heinemann 2002).

As the method for the "crystallization from a solution", concentration method, annealing method, reaction methods (diffusion method or electrolysis method), hydrothermal growth method, fusing agent method and the like can be mentioned. As the solvent to be used, a solvent similar to the aforementioned "inert solvent" can be mentioned.

As the method for the "crystallization from a vapor", gasification methods (sealed tube method or gas stream method), gas phase reaction method, chemical transportation method and the like can be mentioned.

As the method for the "crystallization from a molten form", normal freezing methods (pulling-up method, temperature gradient method or Bridgman method), zone melting methods (zone leveling method or float zone method), special growth methods (VLS method or liquid phase epitaxis method) and the like can be mentioned.

For crystallization of the salt of compound I, crystal precipitation by cooling a solution containing the salt of compound I dissolved therein by heating to generally from 40° C. to the refluxing temperature of the solvent to be used, or crystal precipitation by addition of a poor solvent to a solution containing the salt of compound I dissolved therein (particularly concentrated solution) and the like are utilized. As an analysis method the obtained crystal, an X-ray analysis method is conventionally used. The measurement results of the X-ray analysis are expressed with the Y axis showing the diffraction intensity and the axis of abscissas showing diffraction angles (2θ), wherein 2θ values show dispersion within a certain range even when the same crystal form is measured. To be specific, the dispersion of ±0.2° is the general range. A greater error may be produced depending on the measurement conditions and the like. For comparison of the crystal forms based on the 2θ values, those of ordinary skill in the art compare the crystal forms in consideration of the dispersion. Moreover, the salt and a solvate thereof of the present invention may show some dispersion in the diffraction angle depending on the water content, which is also encompassed in the scope of the present invention.

The salt and a solvate thereof of the present invention (hereinafter to be simply referred to as a salt of the present invention) are superior in stability, and therefore, permit long-term preservation at room temperature. In addition, since they do not require complicated operation during the production step and preservation, and the production of preparation is easy, they are useful as bulk of pharmaceutical products. In view of the high solubility of the salt of the present invention in water, a dosage form having a higher degree of freedom can be developed as a preparation for injection.

When the salt of the present invention is used as a pharmaceutical agent, the salt of the present invention is admixed with a pharmaceutically acceptable carrier (excipient, binder, disintegrant, corrigent, flavor, emulsifier, diluent, dissolution aids etc.) to give a pharmaceutical composition or preparation (tablet, pill, capsule, granule, powder, syrup, emulsion, elixir, suspension, solution, injection, drip infusion, suppository etc.), which can be administered orally or parenterally. A pharmaceutical composition can be processed to a preparation according to a conventional method.

In the present specification, by the parenteral is meant subcutaneous injection, intravenous injection, intramuscular injection, intraperitoneal injection, infusion and the like. A preparation for injection can be produced by a method known in the art. A suppository for rectal administration can be produced by admixing the drug with suitable excipient and the like. As the dosage form of a solid for oral administration, those mentioned above such as powder, granule, tablet, pill, capsule and the like can be mentioned. As a liquid for oral administration, pharmaceutically acceptable emulsion, syrup, elixir, suspension, solution and the like can be mentioned.

The dose of the salt of the present invention is determined in consideration of the age, body weight, general health conditions, sex, diet, administration time, administration method, clearance rate, combination of drugs, and the severity of condition for which the patients are receiving treatments then and other factors. The salt of the present invention shows lower toxicity and can be used safely. While the daily dose varies depending on the condition and body weight of patients, kind of salt, administration route and the like, it is, for example, 0.01 to 100 mg/kg body weight/day, preferably 0.05 to 50 mg/kg body weight/day, for parenteral administration by a subcutaneous, intravenous, intramuscular or rectal route, and 0.01 to 100 mg/kg body weight/day, preferably 0.05 to 50 mg/kg body weight/day for oral administration, which is preferably given once or in several portions a day.

The present invention is explained in detail in the following by referring to Reference Example and Examples, which are not to be construed as limitative.

Unless otherwise specified, anhydrous sodium sulfate or anhydrous magnesium sulfate was used for drying an organic solution for extraction. Column chromatography was performed using a silica gel manufactured by FUJI SILYSIA CHEMICAL LTD.

For thermal analysis (DSC), the temperature (onset value) at the point of intersection of an extension of a linear part before melting with an extension of a linear part during melting in a thermal curve and the temperature (peak top value) at a flexion point near the melting point in the thermal curve are shown. The powder X-ray diffraction pattern (XRD) showed characteristic peaks at angles 2θ (±0.2°). $^1$H-NMR was measured by a 300 MHz Nuclear Magnetic Resonance Spectrometer. The chemical shift of $^1$H-NMR is expressed as relative δ value in parts per million (ppm) using tetramethylsilane (TMS) as an internal standard. The coupling constant shows obvious multiplicity in hertz (Hz), using s (singlet), d (doublet), t (triplet), m (multiplet) and the like. The intensity of absorbance by infrared (IR) spectrometry is expressed using st (strong), m (medium) and w (weak).

While the title compounds in the following Reference Example and Examples are shown as non-solvates, they may take the form of solvates (particularly hydrates) depending on the conditions during preparation and the like.

REFERENCE EXAMPLE 1

3-{(2S,4S)-4-[4-(3-methyl-1-phenyl-1H-pyrazol-5-yl)piperazin-1-yl]pyrrolidin-2-ylcarbonyl}thiazolidine

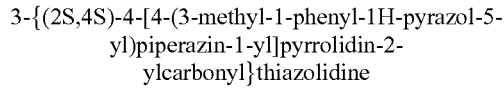

3-{(2S,4S)-1-(1,1-Dimethylethyloxycarbonyl)-4-[4-(3-methyl-1-phenyl-1H-pyrazol-5-yl)piperazin-1-yl]pyrrolidin-2-ylcarbonyl}thiazolidine (25.45 g, synthesized according to the compound described in Example 222 of WO02/14271) was dissolved in dichloromethane (200 mL). Trifluoroacetic acid (50 mL) was added at room temperature, and the mixture was stirred for 19 hrs. The reaction mixture was concentrated under reduced pressure and saturated aqueous sodium hydrogencarbonate solution was added to the residue. The mixture was extracted with chloroform. The extract was washed with saturated brine and dried. The solvent was evaporated under reduced pressure. The residue was purified by silica gel column chromatography to give the title compound as a solid (19.28 g, yield 93%).

Example 1

3-{(2S,4S)-4-[4-(3-methyl-1-phenyl-1H-pyrazol-5-yl)piperazin-1-yl]pyrrolidin-2-ylcarbonyl}thiazolidine 2.5 hydrochloride

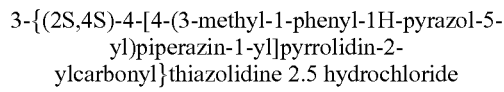

(1) The compound (2.50 g) obtained in Reference Example 1 was dissolved in THF (100 mL). Ethyl acetate solution (3.0 mL, 4 mol/L) of hydrochloric acid was added at room temperature, and the mixture was stirred for 1 hr. The precipitate was collected by filtration and dried under reduced pressure at 50° C. to give a solid (2.69 g).
(2) The product (300 mg) mentioned above was dissolved in a mixed solvent of water (150 μL) and ethanol (1.0 mL) by heating, and the solution was stirred for 1 hr under ice-cooling. The precipitate was collected by filtration and dried under reduced pressure at 50° C. to give the title compound as crystals (144 mg, yield 48%).
XRD: 5.2°, 14.3°, 16.2°, 21.8°, 25.2°.
Anal. calcd for $C_{22}H_{30}N_6OS$ 2.3HCl 2H$_2$O: C, 48.35; H, 6.69; N, 15.38. found: C, 48.02; H, 6.60; N, 15.20.

Example 2

3-{(2S,4S)-4-[4-(3-methyl-1-phenyl-1H-pyrazol-5-yl)piperazin-1-yl]pyrrolidin-2-ylcarbonyl}thiazolidine 2.0 hydrochloride The title compound (60 mg) obtained in Example 1 was suspended in ethyl acetate (3.0 mL), and the suspension was heated under reflux for 13 hrs and allowed to cool to room temperature. The precipitate was collected by filtration and dried with warm air at 40° C. to give the title compound as crystals (50 mg, yield 85%).

XRD: 5.0°, 14.8°, 21.0°, 21.5°, 25.2°.

Anal. calcd for $C_{22}H_{30}N_6OS$ 2.0HCl $H_2O$: C, 51.05; H, 6.62; N, 16.24. found: C, 50.89; H, 6.58; N, 16.12.

Example 3

3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide The compound (5.09 g) obtained in Reference Example 1 was dissolved in ethanol (50.9 mL). 48% Hydrobromic acid (5.03 g) was added at the refluxing temperature, and the mixture was cooled to room temperature over about 1 hr with stirring, and further stirred at room temperature for 1 hr. The precipitate was collected by filtration, washed with ethanol (5 mL) and dried with warm air at 45° C. to give the title compound as crystals (6.76 g).

melting point: 202.0° C. (decomposition)

IR (KBr): 3600-3300 (st), 3116-2850 (st), 2800-2400 (st), 1647 (st), 1592 (m), 1572 (m), 1496 (m), 1450 (m), 1385 (m), 1361 (w), 768 (m), 692 (w).

Example 4

3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide hydrate (1.0 to 2.0 hydrate) Alternative Synthetic Method for the Title Compound of Example 3

(1) To a suspension of sodium triacetoxyborohydride (13.68 kg) in toluene (300 L) were added 1-[4-(3-methyl-1-phenyl-1H-pyrazol-5-yl)piperazine acetate (15.00 kg) and 3-[(2S)-1-(1,1-dimethylethyloxycarbonyl)-4-oxopyrrolidin-2-ylcarbonyl] thiazolidine (14.90 kg), and the mixture was stirred at room temperature for 2.5 hrs. Water (90 L) was added dropwise to the reaction mixture and the mixture was stirred for 0.5 hr. The toluene layer was separated, washed successively with 5% aqueous sodium hydrogencarbonate solution (90 L) and water (90 L) and concentrated to dryness under reduced pressure. IPA (224 L) was added to the residue and 48% hydrobromic acid (25.08 kg) was added dropwise at about 80° C., and the mixture was refluxed for 2.5 hrs. The reaction mixture was allowed to cool, and stirred at about 60° C. for 1.5 hrs, at about 40° C. for 2 hrs, and then at room temperature for 2 hrs. The precipitate was collected by filtration, washed with IPA (30 L) and dried with warm air to give the title compound as a solid (29.76 kg, yield 91%).

(2) To the solid (28.00 kg) obtained in (1) was added ethanol (168 L), and the solid was dissolved by heating. The solution was filtered hot. The reaction vessel was washed with ethanol (28 L), and the filtrate and washing were combined. Water (3 L) was added at 67° C., and the mixture was allowed to cool and stirred at 49° C. for 1 hr and then at 20-15° C. for 1 hr. The precipitate was collected by filtration, washed with ethanol (28 L) and dried with warm air to give the title compound as crystals (25.84 kg, yield 92%), in the form of a hudrate (1.0 to 2.0 hydrate).

XRD: 5.4°, 13.4°, 14.4°, 22.6°, 26.5°.

Example 5

3-{(2S,4S)-4-[4-(3-methyl-1-phenyl-1H-pyrazol-5-yl)piperazin-1-yl]pyrrolidin-2-ylcarbonyl}thiazolidine 2.0 hydrobromide (1) The title compound (130 g) obtained in Example 4 was added to water (260 mL) at room temperature, and the compound was dissolved by stirring. The precipitate was collected by filtration and dried to give 3.5 hydrate (53.58 g) of Form A crystal of the title compound.

XRD: 5.7°, 7.7°, 11.3°, 16.2°, 17.0°.

(2) The hydrate (8.5 g) of Form A crystal obtained in (1) was added to ethanol (100 mL, containing 2% water) at 28-30° C., and the hydrate was dissolved by stirring. The precipitate was collected by filtration and dried to give a hydrate (4.56 g) of Form B crystal of the title compound.

XRD: 5.2°, 10.4°, 19.1°, 19.8°, 20.7°.

(3) The hydrate (8.5 g) of Form A crystal obtained in (1) added to ethanol (100 mL, containing 2% water) at 15-18° C., and the hydrate was dissolved by stirring. The precipitate was collected by filtration and dried to give a hydrate (6.21 g) of Form C crystal of the title compound.

XRD: 5.5°, 13.4°, 14.3°, 21.4°, 26.7°.

Example 6

3-{(2S,4S)-4-[4-(3-methyl-1-phenyl-1H-pyrazol-5-yl)piperazin-1-yl]pyrrolidin-2-ylcarbonyl}thiazolidine n nitrate The compound (200 mg) obtained in Reference Example 1 was dissolved in ethanol (2 mL). Nitric acid (0.07 mL) was added at room temperature, and the mixture was stirred for 4 hrs. The solvent was evaporated and ethyl acetate (3 mL) was added. The precipitate was collected by filtration and dried under reduced pressure to give the title compound as an amorphous form (208 mg, yield 80%). (n is 1 to 3)

Example 7

3-{(2S,4S)-4-[4-(3-methyl-1-phenyl-1H-pyrazol-5-yl)piperazin-1-yl]pyrrolidin-2-ylcarbonyl}thiazolidine 3 mesylate (1) The compound (2.64 g) obtained in Reference Example 1 was dissolved in THF (25 mL). Mesyl acid (1.32 mL) was added at room temperature and the mixture was stirred for 1.5 hrs. The precipitate was collected by filtration and dried under reduced pressure to give crystals (3.52 g, yield 80%).

(2) The above-mentioned crystals (1.76 g) were dissolved in ethanol (10 mL) by heating and the solution was stirred at room temperature for 17 hrs. The precipitate was collected by filtration and dried under reduced pressure to give the title compound as crystals (1.26 g, yield 72%).

DSC: 193-197° C.

Anal. calcd for $C_{22}H_{30}N_6OS$ $3CH_4O_3S$ $H_2O$: C, 40.97%; H, 6.05%; N, 11.47%. found: C, 41.05%; H, 5.72%; N, 11.48%.

Example 8

3-{(2S,4S)-4-[4-(3-methyl-1-phenyl-1H-pyrazol-5-yl)piperazin-1-yl]pyrrolidin-2-ylcarbonyl}thiazolidine 2 mesylate (1) The compound (7.96 g) obtained in Reference Example 1 was dissolved in IPA (60 mL). A solution of mesyl acid (3.59 g) in IPA (20 mL) was added at room temperature, and the mixture was stirred for 2 hrs. The precipitate was collected by filtration and dried under reduced pressure to give a solid (9.03 g, yield 78%).
(2) The above-mentioned solid (1000 mg) was suspended in acetonitrile (20 mL), and the suspension was heated under reflux for 30 min and allowed to cool to room temperature. The precipitate was collected by filtration to give a solid (847 mg). The solid (813 mg) was suspended in acetonitrile (16 mL), and the suspension was heated under reflux for 1 hr and allowed to cool to room temperature. The precipitate was collected by filtration and dried under reduced pressure to give the title compound as crystals (690 mg, yield 72%).
DSC: 213-216° C.
Anal. calcd for $C_{22}H_{30}N_6OS\ 2CH_4O_3S\ 0.5H_2O$: C, 45.92; H, 6.26; N, 13.39. found: C, 45.96; H, 6.17; N, 13.37.

Example 9

3-{(2S,4S)-4-[4-(3-methyl-1-phenyl-1H-pyrazol-5-yl)piperazin-1-yl]pyrrolidin-2-ylcarbonyl}thiazolidin 2 tosylate (1) The compound (5.28 g) obtained in Reference Example 1 was dissolved in IPA (30 mL). Tosyl acid monohydrate (4.94 g) was added at room temperature and the mixture was stirred for 1.5 hrs. The precipitate was collected by filtration and dried under reduced pressure to give Form A crystal of the title compound (7.84 g, yield 82%).
XRD: 5.3°, 6.0°, 14.8°, 16.4°, 20.8°.
Anal. calcd for $C_{22}H_{30}N_6OS\ 2C_7H_8O_3S\ 0.25H_2O$: C, 55.76%; H, 6.04%; N, 10.84%. found: C, 55.71%; H, 6.06%; N, 10.80%.
(2) The product (1.5 g) mentioned above was dissolved in water (20 mL) by heating and the solution was stirred at room temperature for 1 hr. The precipitate was collected by filtration and dried under reduced pressure to give Form B crystal of the title compound (1.2 g, yield 80%).
XRD: 5.7°, 11.4°, 14.0°, 18.2°, 19.7°.
Anal. calcd for $C_{22}H_{30}N_6OS\ 2C_7H_8O_3S\ 0.5H_2O$: C, 55.43%; H, 6.07%; N, 10.77%. found: C, 55.14%; H, 6.09%; N, 10.73%.
(3) The resultant product (1.4 g) obtained in (1) was suspended in IPA (100 mL), and the suspension was heated under reflux for 1 hr and allowed to cool to room temperature. The precipitate was collected by filtration and dried under reduced pressure to give Form C crystal of the title compound (1.1 g, yield 81%).
DSC: 227-230° C.
XRD: 4.7°, 5.7°, 11.3°, 19.8°, 21.4°.
Anal. calcd for $C_{22}H_{30}N_6OS\ 2C_7H_8O_3S$: C, 56.08%; H, 6.01%; N, 10.90%. found: C, 55.83%; H, 6.11%; N, 10.87%.

Example 10

3-{(2S,4S)-4-[4-(3-methyl-1-phenyl-1H-pyrazol-5-yl)piperazin-1-yl]pyrrolidin-2-ylcarbonyl}thiazolidine 2 besylate (1) The compound (4.36 g) obtained in Reference Example 1 was dissolved in IPA (70 mL). Besyl acid (3.78 g) was added at room temperature and the mixture was stirred for 1 hr. The precipitate was collected by filtration and dried under reduced pressure to give Form A crystal of the title compound (6.05 g, yield 80%).
XRD: 5.7°, 8.9°, 19.4°, 20.2°, 21.6°.
$^1$H-NMR (DMSO-$d_6$): δ 1.82-2.10 (1H, m), 2.17 (3H, s), 2.60-4.20 (16H, m), 4.11-4.72 (3H, m), 5.91 (1H, s), 7.31-7.35 (7H, m), 7.45-7.50 (2H, m), 7.59-7.62 (4H, m), 7.75 (2H, d, J=7.8 Hz).
(2) The product (1.81 g) mentioned above was dissolved in ethanol (25 mL) by heating and the solution was stirred at room temperature for 1 hr. The precipitate was collected by filtration and dried under reduced pressure to give Form B crystal of the title compound (1.25 g, yield 69%).
XRD: 5.6°, 6.7°, 19.3°, 22.9°, 23.2°.
Anal. calcd for $C_{22}H_{30}N_6OS\ 2C_6H_6O_3S$: C, 54.97%; H, 5.70%; N, 11.31%. found: C, 54.67%; H, 5.61%; N, 11.25%.

Example 11

3-{(2S,4S)-4-[4-(3-methyl-1-phenyl-1H-pyrazol-5-yl)piperazin-1-yl]pyrrolidin-2-ylcarbonyl}thiazolidine 2 naphthalene-1-sulfonate (1) The compound (4.01 g) obtained in Reference Example 1 was dissolved in THF (80 mL). A solution of naphthalene-1-sulfonic acid (4.11 g) in THF (40 mL) was added at room temperature, and the mixture was stirred for 3 hrs. The precipitate was collected by filtration and dried under reduced pressure to give a solid (5.96 g, yield 75%).
(2) The above-mentioned solid (500 mg) was dissolved in ethanol (25 mL) by heating and the solution was refluxed for 30 min and allowed to cool to room temperature. The precipitate was collected by filtration and dried under reduced pressure to give the title compound as crystals (445 mg, yield 89%).
DSC: 184-189° C.
Anal. calcd for $C_{22}H_{30}N_6OS\ 2C_{10}H_8O_3S\ 0.25H_2O$: C, 59.52; H, 5.52; N, 9.92. found: C, 59.32; H, 5.46; N, 9.88.

Example 12

3-{(2S,4S)-4-[4-(3-methyl-1-phenyl-1H-pyrazol-5-yl)piperazin-1-yl]pyrrolidin-2-ylcarbonyl}thiazolidine 2 naphthalene-2-sulfonate (1) The compound (2.57 g) obtained in Reference Example 1 was dissolved in ethyl acetate (50 mL). A solution of naphthalene-2-sulfonic acid monohydrate (2.86 g) in ethyl acetate (25 mL) was added at room temperature, and the mixture was stirred for 12 hrs. The precipitate was collected by filtration and dried under reduced pressure to give a solid (4.60 g, yield 91%).
(2) The above-mentioned solid (500 mg) was dissolved in ethanol (25 mL) by heating and the solution was stirred at room temperature. The precipitate was collected by filtration and dried under reduced pressure to give the title compound as crystals (372 mg, yield 74%).
DSC: 205-211° C.
Anal. calcd for $C_{22}H_{30}N_6OS\ 2C_{10}H_8O_3S\ 0.75H_2O$: C, 58.89; H, 5.59; N, 9.81. found: C, 58.96; H, 5.49; N, 9.76.

Example 13

3-{(2S,4S)-4-[4-(3-methyl-1-phenyl-1H-pyrazol-5-yl)piperazin-1-yl]pyrrolidin-2-ylcarbonyl}thiazolidine gallate The compound (4.05 g) obtained in Reference Example 1 was dissolved in IPA (30 mL). An IPA solution (30 mL) of gallic acid monohydrate (1.96 g) was added at room temperature, and the mixture was stirred for 1 hr. The precipitate was collected by filtration and dried under reduced pressure to give the title compound as a solid (4.84 g, yield 85%).

$^1$H-NMR (DMSO-d$_6$): δ 1.43-1.62 (1H, m), 2.14 (3H, s), 2.19-3.08 (13H, m), 3.55-3.96 (4H, m), 4.20-4.69 (2H, m), 5.91 (1H, s), 7.31-7.35 (7H, m), 7.45-7.50 (2H, m), 7.59-7.62 (4H, m), 7.75 (2H, d, J=7.8 Hz).

Example 14

3-{(2S,4S)-4-[4-(3-methyl-1-phenyl-1H-pyrazol-5-yl)piperazin-1-yl]pyrrolidin-2-ylcarbonyl}thiazolidine 2 (+)-camphorsulfonate (1) The compound (3.00 g) obtained in Reference Example 1 was dissolved in a mixed solvent of THF (72.5 mL) and t-butyl methyl ether (52.5 mL). (+)-Camphorsulfonic acid (3.25 g) was added at room temperature and the mixture was stirred for 5 hrs. The precipitate was collected by filtration and dried under reduced pressure to give a solid (5.65 g, yield 90%).

(2) The above-mentioned solid (650 mg) was dissolved in a mixed solvent of ethanol (7.0 mL) and diethyl ether (15.0 mL) by heating, and the solution was stirred overnight at room temperature. The precipitate was collected by filtration and dried with warm air to give the title compound containing ethanol as crystals (380 mg, yield 58%).
TG/DTA: 142-156° C., 200-205° C.
Anal. calcd for $C_{22}H_{30}N_6OS$ $2C_{10}H_{16}O_4S$ $0.22C_2H_6O$ $2.5H_2O$: C, 53.66; H, 7.29; N, 8.86. found: C, 53.82; H, 7.27; N, 8.88.

Example 15

3-{(2S,4S)-4-[4-(3-methyl-1-phenyl-1H-pyrazol-5-yl)piperazin-1-yl]pyrrolidin-2-ylcarbonyl}thiazolidine 2 (−)-camphorsulfonate The compound (3.00 g) obtained in Reference Example 1 was dissolved in a mixed solvent (70 mL, THF/t-butyl methyl ether=1:3). A solution of (−)-camphorsulfonic acid (3.25 g) in a mixed solvent (THF/t-butyl methyl ether=1:3) was added at room temperature, and the mixture was stirred for 1 hr. The precipitate was collected by filtration and dried under reduced pressure to give the title compound as a solid (5.66 g, yield 91%).

Example 16

3-{(2S,4S)-4-[4-(3-methyl-1-phenyl-1H-pyrazol-5-yl)piperazin-1-yl]pyrrolidin-2-ylcarbonyl}thiazolidine 2 maleate (1) The compound (1.70 g) obtained in Reference Example 1 was dissolved in ethanol (50 mL). Maleic acid (0.98 g) was added at room temperature, and the mixture was stirred for 1 hr. The precipitate was collected by filtration and dried under reduced pressure to give Form A crystal of the title compound (1.87 g, yield 71%).
Anal. calcd for $C_{22}H_{30}N_6OS$ $2C_4H_4O_4$: C, 54.70%; H, 5.81%; N, 12.76%. found: C, 54.42%; H, 5.76%; N, 12.57%.
XRD: 8.6°, 15.8°, 17.8°, 18.6°, 23.4°.

(2) The above-mentioned crystal (3.0 g) was dissolved in water (15 mL) by heating and the solution was stirred at room temperature for 1 hr. The precipitate was collected by filtration and dried under reduced pressure to give Form B crystal of the title compound (1.83 g, yield 61%).
XRD: 5.9°, 13.4°, 16.3°, 17.6°, 23.9°.
Anal. calcd for $C_{22}H_{30}N_6OS$ $2C_4H_4O_4$ $2H_2O$: C, 51.86%; H, 6.09%; N, 12.10%. found: C, 51.80%; H, 5.84%; N, 12.10%.

Example 17

3-{(2S,4S)-4-[4-(3-methyl-1-phenyl-1H-pyrazol-5-yl)piperazin-1-yl]pyrrolidin-2-ylcarbonyl}thiazolidine 2 fumarate (1) The compound (1.50 g) obtained in Reference Example 1 was dissolved in ethanol (20 mL). A solution of fumaric acid (814 mg) in ethanol (25 mL) was added at room temperature, and the mixture was stirred at room temperature for 1 hr and then under ice-cooling for 1 hr. ⅓ volume of the reaction solvent was evaporated. The precipitate was collected by filtration and dried under reduced pressure to give a solid (1.77 g, yield 77%).

(2) The solid (200 mg) obtained in (1) was suspended in acetonitrile (5 mL), and the suspension was heated under reflux for 4 hrs and allowed to cool to room temperature. The precipitate was collected by filtration to give the title compound as crystals (141 mg, yield 71%). Since the crystal showed two endothermic peaks by DSC, the crystal was assumed to be a mixture of two crystal forms (Form A, Form B), or to shift from Form A to Form B due to the heat.
DSC: 128-(135 or 142)° C.
XRD: 3.1°, 15.2°, 17.4°, 23.4°, 25.5°.
Anal. calcd for $C_{22}H_{30}N_6OS$ $2C_4H_4O_4$: C, 54.70; H, 5.81; N, 12.76. found: C, 54.40; H, 5.88; N, 12.63
$^1$H-NMR (DMSO-d$_6$): δ 1.50-1.78 (1H, m), 2.14 (3H, m), 2.37-3.90 (16H, m), 4.10-4.72 (3H, m), 5.79 (1H, s), 6.57 (4H, s), 7.27 (1H, t, J=7.2 Hz), 7.46 (2H, t, J=8.1 Hz), 7.74 (2H, d, J=7.7 Hz).

(3) The solid (200 mg) obtained in (1) was dissolved in water (2 mL) and the solution was stirred at room temperature. The precipitate was collected by filtration to give the title compound as crystals (47.5 mg, yield 24%). The crystal showed a powder X-ray pattern different from that of the crystal obtained in (2).
XRD: 9.4°, 17.8°, 19.6°, 21.0°, 23.5°, 24.3°.

Example 18

3-{(2S,4S)-4-[4-(3-methyl-1-phenyl-1H-pyrazol-5-yl)piperazin-1-yl]pyrrolidin-2-ylcarbonyl}thiazolidine 1.6 sulfate The compound (2.00 g) obtained in Reference Example 1 was dissolved in THF (40 mL). Aqueous sulfuric acid solution (14.5 mL, 0.5 mol/L) was added at room temperature, and the mixture was stirred for 0.5 hr. The precipitate was collected by filtration and dried under reduced pressure to give the title compound as a solid (2.57 g, yield 94%).
Anal. calcd for $C_{22}H_{30}N_6OS$ $1.6H_2O_4S$ $2H_2O$: C, 42.65; H, 6.05; N, 13.57. found: C, 42.56; H, 5.67; N, 13.44.

Example 19

3-{(2S,4S)-4-[4-(3-methyl-1-phenyl-1H-pyrazol-5-yl)piperazin-1-yl]pyrrolidin-2-ylcarbonyl}thiazolidine 2 L-tartrate (1) The compound (1.17 g) obtained in Reference Example 1 was dissolved in IPA (30 mL). L-Tartaric acid (823 mg)

was added at room temperature and the mixture was stirred for 3 hrs. The precipitate was collected by filtration and dried under reduced pressure to give crystals (1.55 g, yield 78%).

(2) The product (254 mg) mentioned above was suspended in ethyl acetate (10 mL), and the suspension was heated under reflux for 1.5 hrs and allowed to cool to room temperature. The precipitate was collected by filtration and dried under reduced pressure to give the title compound as crystals (250 mg, yield 98%).

$^1$H-NMR (DMSO-d$_6$): δ 1.50-1.69 (1H, m), 2.14 (3H, m), 2.40-3.90 (16H, m), 4.08 (2H, s), 4.30-4.70 (3H, m), 5.79 (1H, s), 7.27 (1H, t, J=7.3 Hz), 7.46 (2H, m), 7.73 (2H, d, J=7.8 Hz).

Example 20

3-{(2S,4S)-4-[4-(3-methyl-1-phenyl-1H-pyrazol-5-yl)piperazin-1-yl]pyrrolidin-2-ylcarbonyl}thiazolidine m phosphate The compound (100 mg) obtained in Reference Example 1 was dissolved in THF (2 mL). Phosphoric acid (0.032 mL) was added at room temperature and the mixture was stirred for 1 hr. The precipitate was collected by filtration and dried under reduced pressure to give the title compound as an amorphous form (144 mg, yield 93%). (m is 1 to 3)

EXPERIMENTAL EXAMPLE 1

Measurement of Powder X-ray Diffraction

The powder X-ray diffraction of the title compounds of Examples 4 and 5 was measured under the following measurement conditions.
apparatus: XRD-6000 manufactured by Shimadzu Corporation
anticathode: Cu
monochrometer: Graphite
tube voltage: 40 kV
tube electric current: 40 mA
divergence slit: 1°
receiving slit: 0.15 mm
scatter slit: 1°
scanning range: 2-40° (2θ)
sample rpm: 60 rpm The measurement results of the powder X-ray diffraction of the title compound of Example 4 are shown in FIG. 1.

Figure 2:
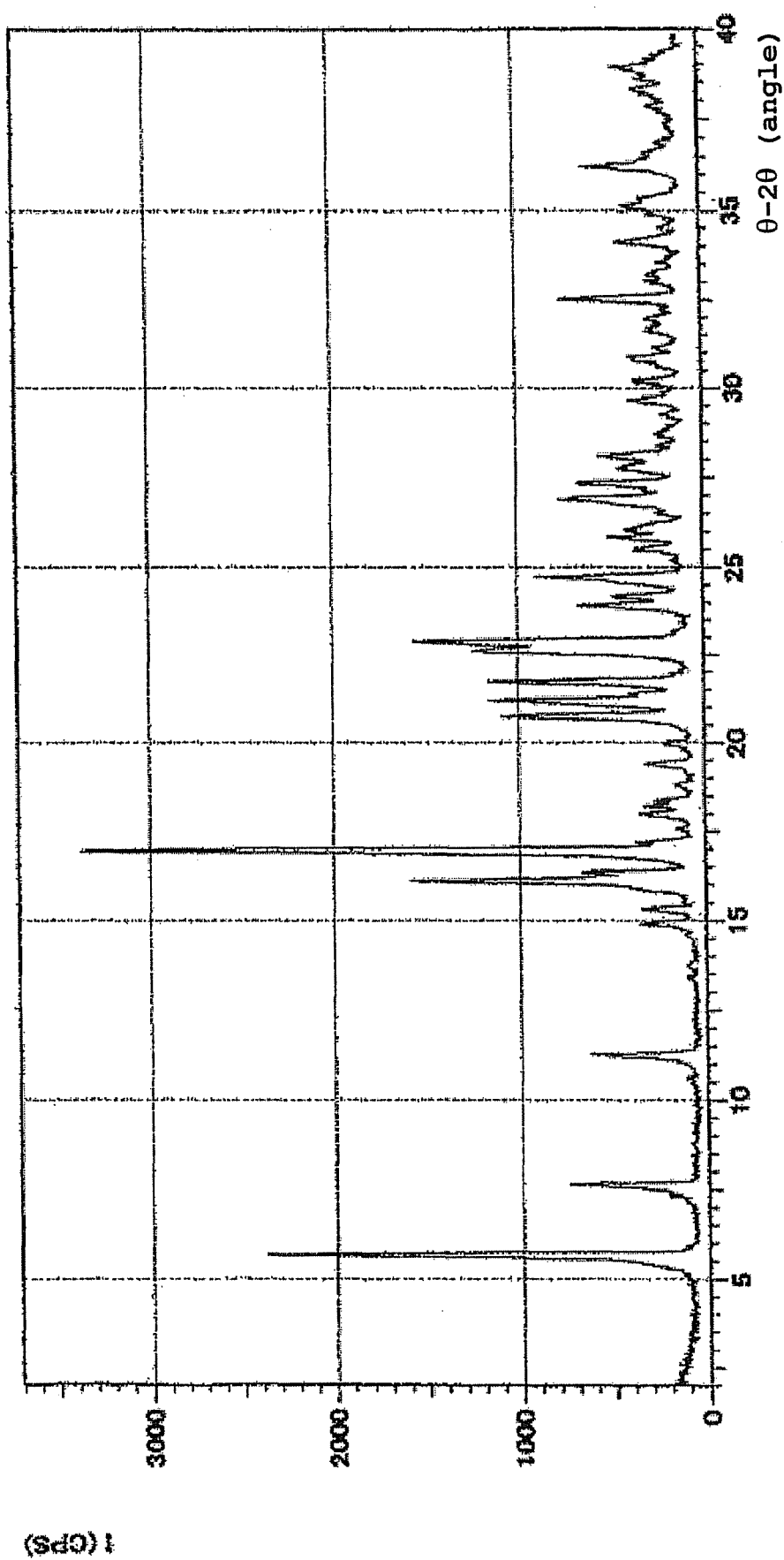
FIG. 2 shows the measurement results of the powder X-ray diffraction of the compound of Example 5, (1), wherein the Y axis shows diffraction intensity and the axis of abscissas shows diffraction angle (2θ).

The measurement results of the powder X-ray diffraction of Form A crystal of the title compound of Example 5 are shown in FIG. 2.

Figure 3:
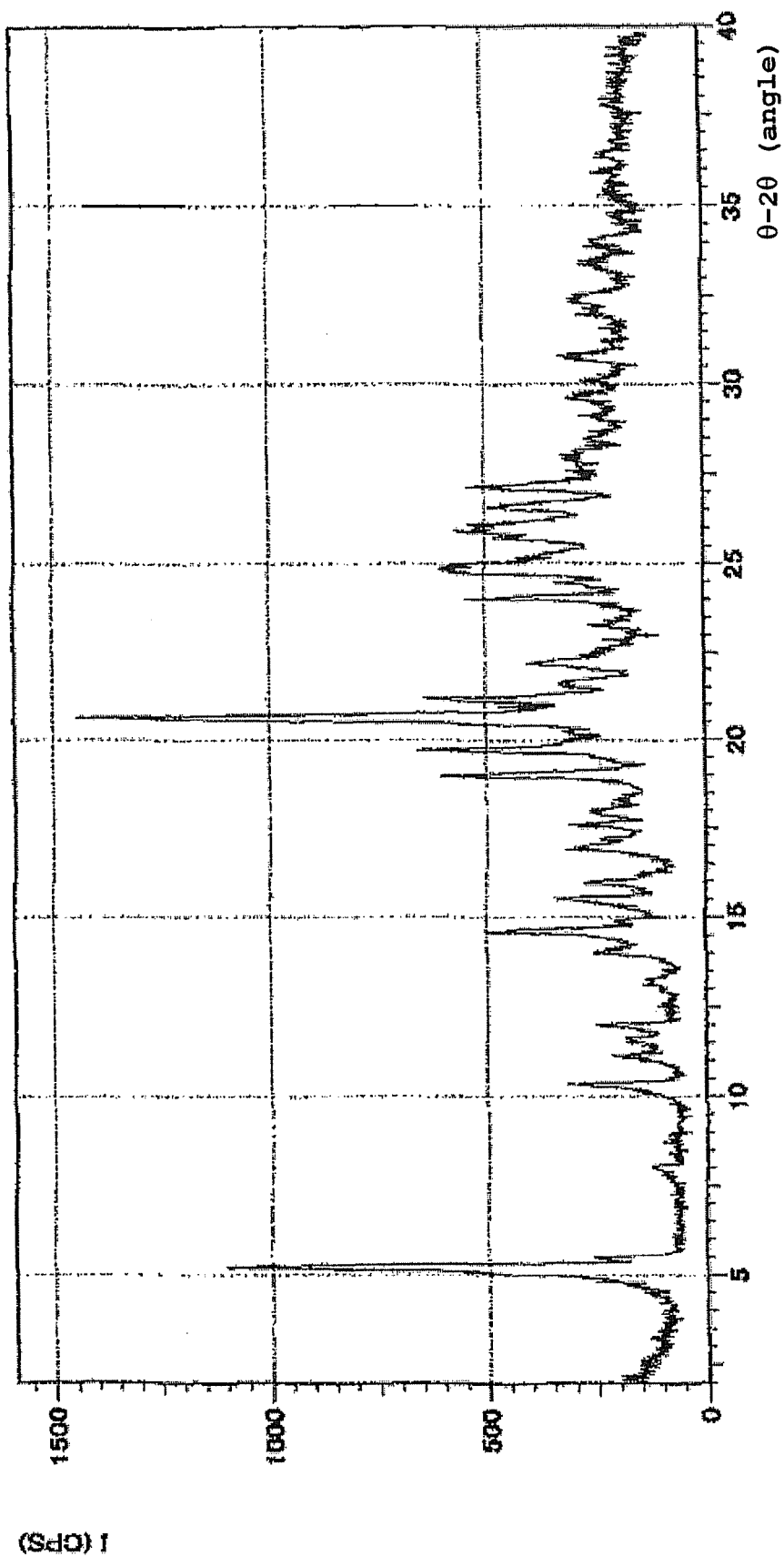
FIG. 3 shows the measurement results of the powder X-ray diffraction of the compound of Example 5, (2), wherein the Y axis shows diffraction intensity and the axis of abscissas shows diffraction angle (2θ).

The measurement results of the powder X-ray diffraction of Form B crystal of the title compound of Example 5 are shown in FIG. 3.

Figure 4:
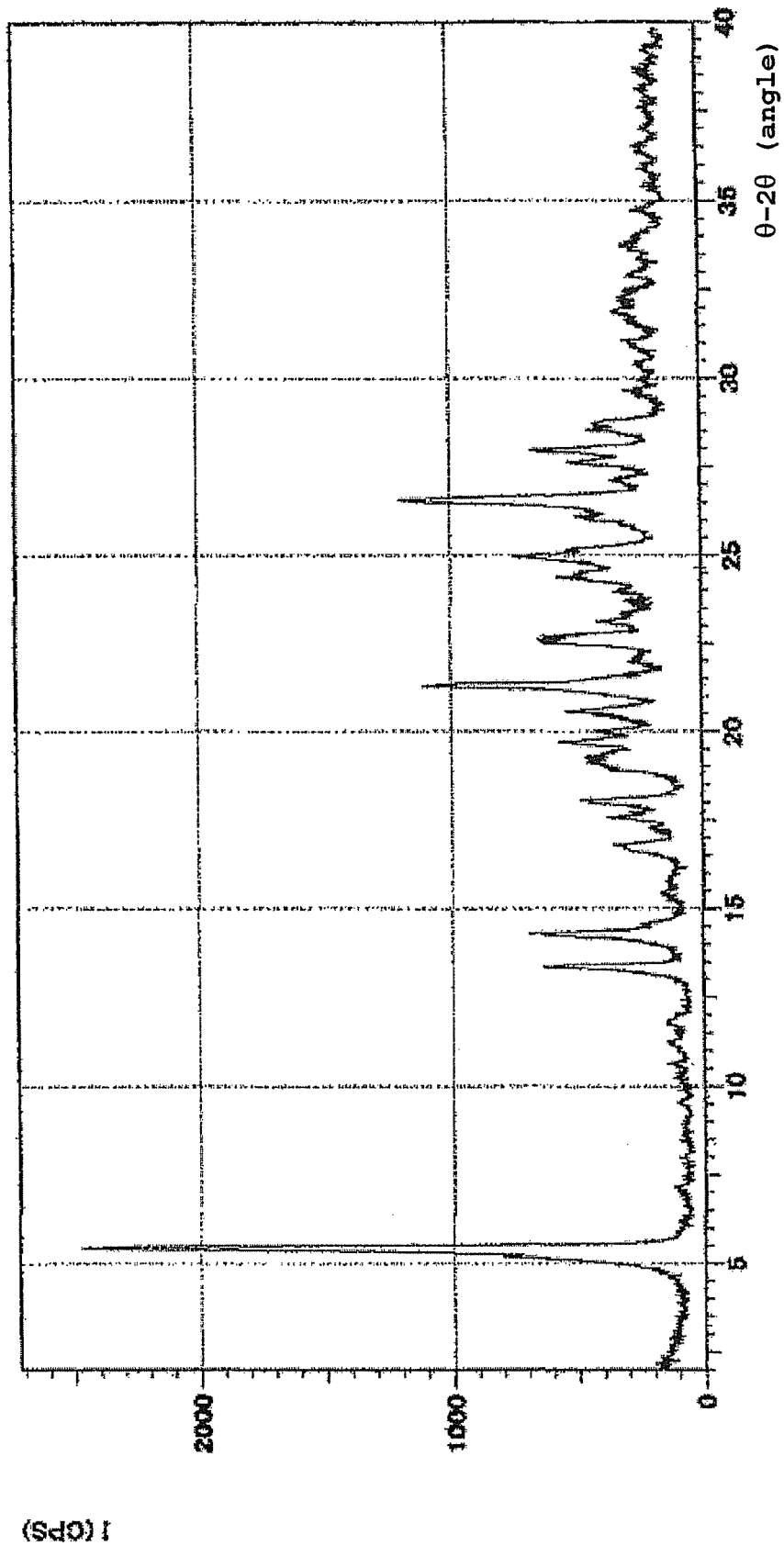
FIG. 4 shows the measurement results of the powder X-ray diffraction of the compound of Example 5, (3), wherein the Y axis shows diffraction intensity and the axis of abscissas shows diffraction angle (2θ).

The measurement results of the powder X-ray diffraction of Form C crystal of the title compound of Example 5 are shown in FIG. 4.

EXPERIMENTAL EXAMPLE 2

Measurement of Hygroscopicity

Figure 5:
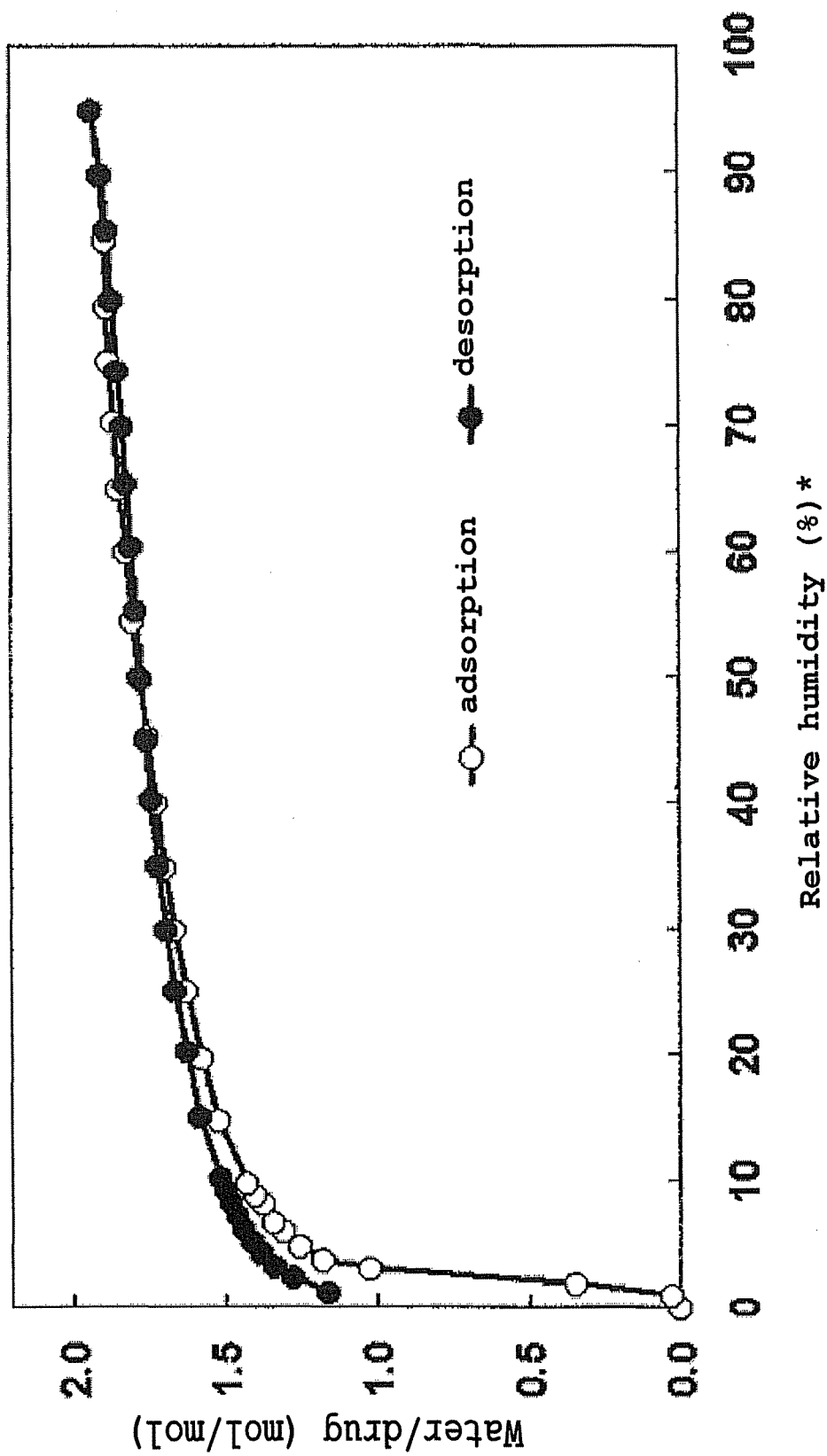
FIG. 5 shows the measurement results of the hygroscopicity of the title compound of Example 3, wherein -○- plots the adsorption of water to the compound at the humidity of the axis of abscissas, and -●- plots the desorption of water to the compound at the humidity of the axis of abscissas.

The hygroscopicity of the title compound of Example 3 was measured under the following conditions using a moisture adsorption measurement apparatus.
apparatus: MB-300G manufactured by VTI
measurement temperature: 25° C.
measurement range: 0-95% RH The measurement results of hygroscopicity are shown in FIG. 5.

The title compound of Example 3 was subjected to a moisture adsorption measurement using a reduced pressure type moisture adsorption measurement apparatus. As a result, the compound was found to have maintained water corresponding to a 1.8 hydrate at 50% RH, and be almost completely dry at 0% RH.

EXPERIMENTAL EXAMPLE 3

Measurement of Solubility
(1) Measurement of Solubility in Water

As a measurement method, visual observation was used, which permits convenient evaluation of rough solubility with a small amount of sample. The temperature during measurement was 37° C. About 3 mg of the title compound of Example 3 was taken in a sample bottle with a screw cap, a test solution (0.15 mL) was added and the cap was screwed tightly thereon. The sample was ultrasonicated for 1 min to give a dispersion, which was placed in a shaking-type thermostat water bath stabilized at 37° C. and shaken for 1 hr. Then, dissolution was confirmed by visual observation. As a result, the solubility of the title compound of Example 3 in water was not less than 20 mg/mL at 37° C.

(2) Measurement of Solubility at pH 9-13

Using 0.2 mol/L NaOH/0.1 mol/L NaCl mixed solution as a test solution, the solubility of the title compound of Example 3 having a pH of 9-13 at room temperature was analyzed by liquid chromatography (HPLC) (n=3). As a result, the solubility was 6.4 mg/mL-8.4 mg/mL. From the foregoing, the solubility of the title compound of Example 3 was concluded to be about 7 mg/mL.

TABLE 1

Solubility of title compound of Example 3 at each pH (25° C.)

| pH | Solubility (mg/mL) |
|---|---|
| 8.81 | 8.4 |
| 11.94 | 7.2 |
| 11.98 | 7.9 |
| 12.10 | 7.2 |
| 12.26 | 7.8 |
| 12.70 | 6.4 |
| 12.99 | 6.8 |

INDUSTRIAL APPLICABILITY

A salt of compound I or a solvate thereof, and novel polymorphic crystals thereof have one or more properties selected from improved stability, improved hygroscopicity (deliquescency), rapid isolation from solvent and easy production of preparation, and promote the development of compound I as a pharmaceutical product.

This application is based on application No. 2005-041851 filed in Japan, the contents of which are incorporated hereinto by reference.

The invention claimed is:

1. The compound that is either 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide or a hydrate thereof.

2. A method of producing 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide or a hydrate thereof, which comprises eliminating 1,1-dimethylethyloxycarbonyl from 3-{(2S,4S)-1-(1,1-dimethylethyloxycarbonyl)-4-[4-(3-methyl-1-phenyl-1H-pyrazol-5-yl)piperazin-1-yl]pyrrolidin-2-ylcarbonyl}thiazolidine with hydrobromic acid, and simultaneously forming a salt.

3. A method of producing 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide or a hydrate thereof, which comprises crystallizing 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide from water and/or a solvent selected from ethanol, 1-propanol, 2-propanol, ethyl acetate, and acetone.

4. The method of claim 2, wherein the hydrate is a 1.0 to 2.0 hydrate.

5. The method of claim 3, wherein the hydrate is a 1.0 to 2.0 hydrate.

6. The compound of claim 1, which is a hydrate of 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide.

7. The compound of claim 6, wherein the hydrate is a 1.0 to 2.0 hydrate.

8. The compound of claim 7, which has peaks at diffraction angles represented by 2θ of 5.4°, 13.4° and 14.4° (each ±0.2°) in a powder X-ray diffraction pattern.

* * * * *